United States Patent [19]
Komi

[11] Patent Number: 4,979,496
[45] Date of Patent: Dec. 25, 1990

[54] ENDOSCOPE FOR BILE DUCT AND PANCREATIC DUCT

[75] Inventor: Shuji Komi, Saitama, Japan

[73] Assignee: Fuji Photo Optical Co., Ltd., Omiya, Japan

[21] Appl. No.: 332,859

[22] Filed: Apr. 3, 1989

[30] Foreign Application Priority Data

Apr. 5, 1988 [JP] Japan .................................. 63-83587
Apr. 5, 1988 [JP] Japan .................................. 63-83588
Apr. 5, 1988 [JP] Japan .................................. 63-83589
Apr. 5, 1988 [JP] Japan .................................. 63-83590

[51] Int. Cl.$^5$ ............................................. A61B 1/00
[52] U.S. Cl. ....................................................... 128/4
[58] Field of Search .................................... 128/4, 6, 7

[56] References Cited

U.S. PATENT DOCUMENTS 3,643,653 2/1972 Takahashi et al. ...................... 128/6
4,586,491 5/1986 Carpenter .............................. 128/6

Primary Examiner—William H. Grieb
Attorney, Agent, or Firm—Jordan and Hamburg

[57] ABSTRACT

An endoscope for bile duct and pancreatic duct of double scope system including a mother endoscope having an insertion unit to be inserted into duodenum and a daughter endoscope having an insertion unit to be inserted via papilla through a forceps channel of the insertion unit.

The endoscope is provided with a flexible guide tube to be inserted into bile duct and pancreatic duct through a forceps channel from the insertion hole of the mother endoscope, and the insertion unit of the daughter endoscope can be inserted into this guide tube. Further, the endoscope is provided with a core bar, which is removably mounted on one end of the guide tube and is designed to be of such length that its tip does not protrude from the tip of the guide tube when it is inserted into the guide tube.

4 Claims, 13 Drawing Sheets

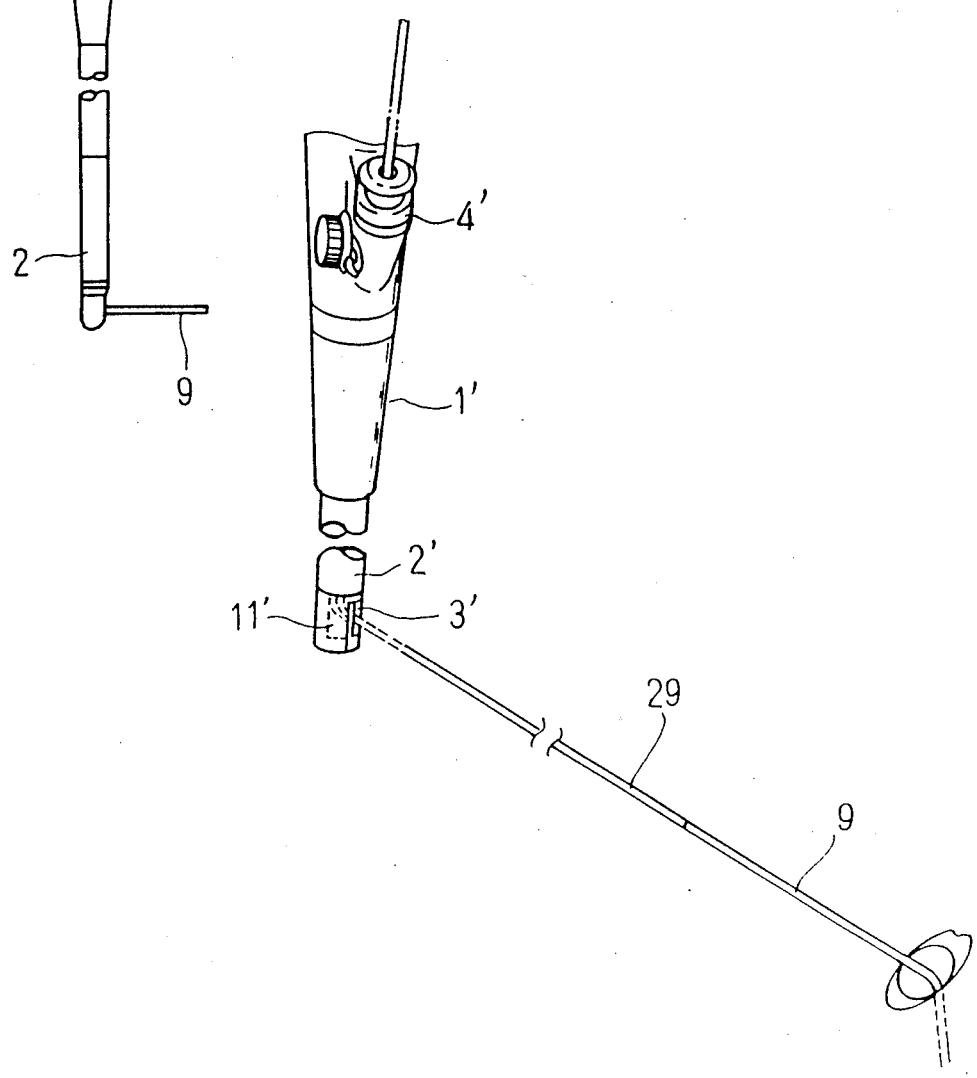

FIG. 14
FIG. 15
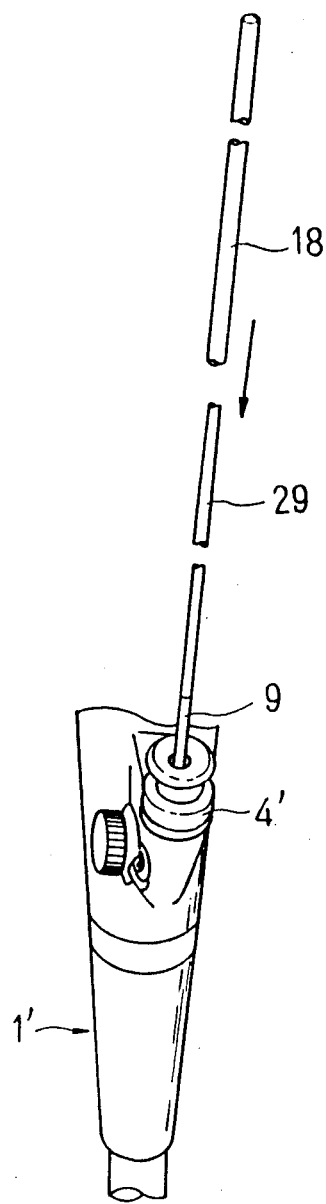
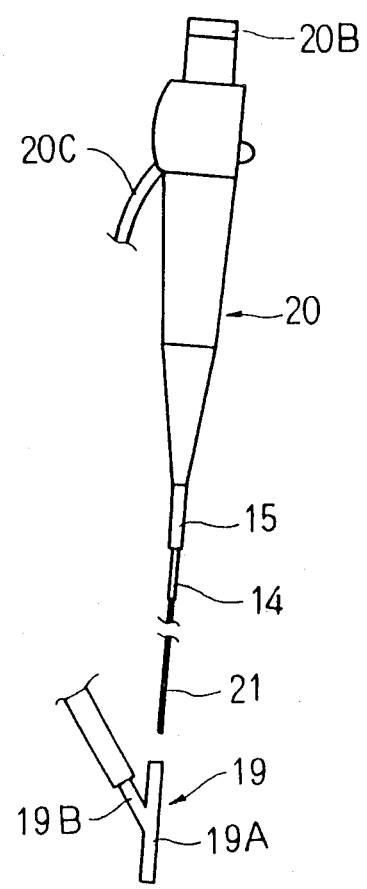
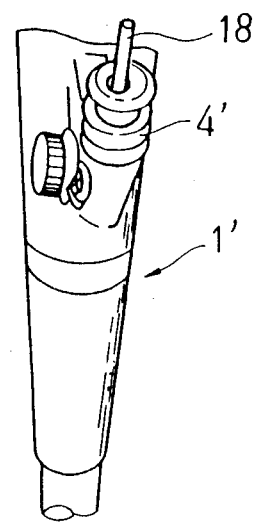

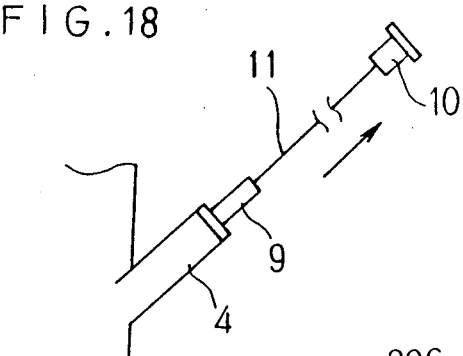
FIG. 18
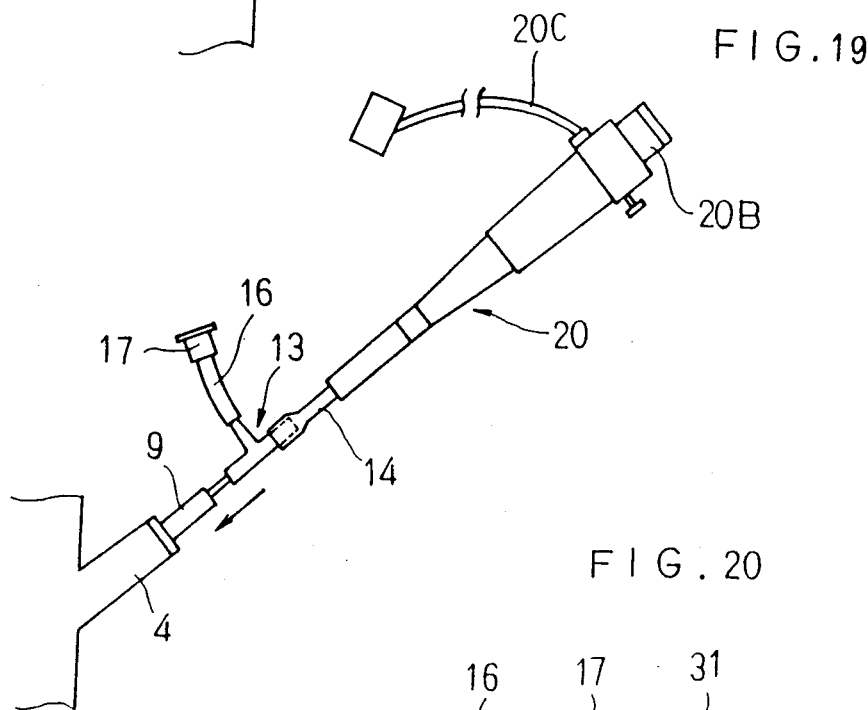
FIG. 19
FIG. 20
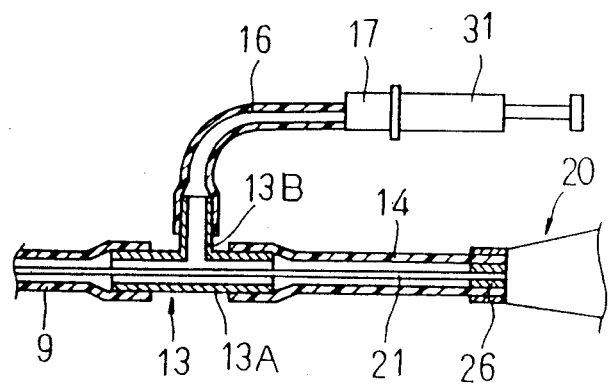

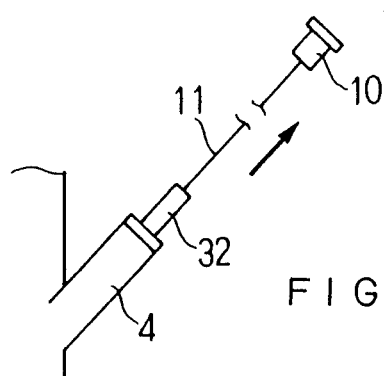
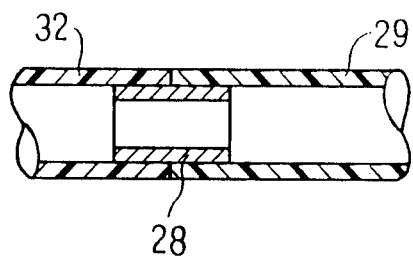
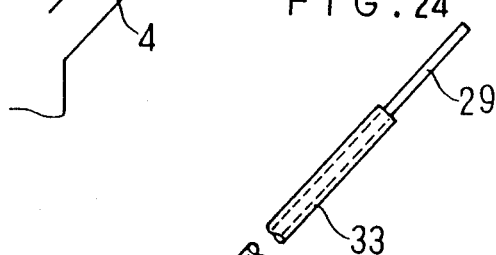
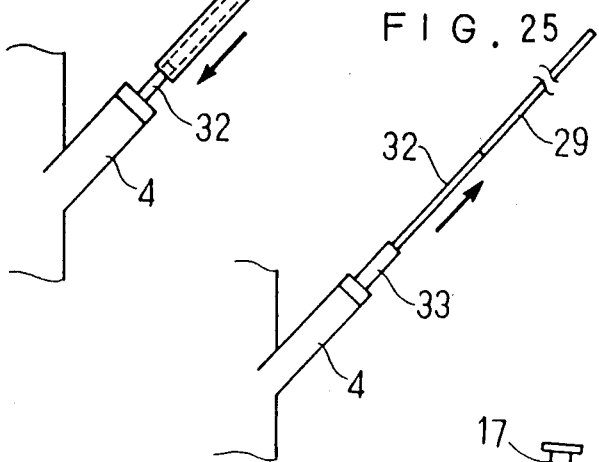
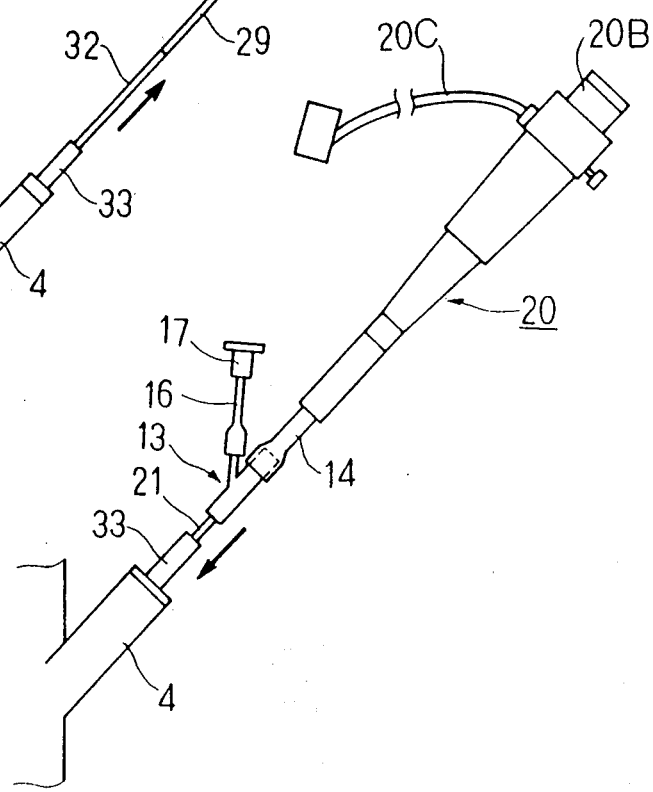

ENDOSCOPE FOR BILE DUCT AND PANCREATIC DUCT

BACKGROUND OF THE INVENTION

The present invention relates to an endoscope for bile duct and pancreatic duct for non-invasive endoscopic observation of bile duct and pancreatic duct.

An endoscope of double-scope system is already known. This consists of a mother endoscope having an insertion unit, which can be inserted into duodenum, and of a daughter endoscope having an insertion unit, which can be introduced by transpapillary insertion through a forceps channel of the above insertion unit. In such system of endoscope, the interior of the bile duct and pancreatic duct can be observed by introducing the insertion unit of the daughter endoscope directly into papilla through forceps channel of the mother endoscope. However, it is necessary to have perfusion to clean up the interior of the region to be observed for perfect examination of bile duct and pancreatic duct. For this purpose, the insertion unit of the daughter endoscope must have a path, through which physiological saline for perfusion can be sent, and, accordingly, the insertion unit must have larger diameter. The tip of the insertion unit of such daughter endoscope cannot be inserted conveniently into papilla unless it is bent toward the desired direction. Consequently, it is designed in such manner that the tip can be bent upward or downward.

In the conventional double scope system, the tip of the insertion unit of the daughter endoscope is directly inserted into papilla. To ensure the positive insertion, the tip must be bent. Also, it is necessary to provide a path to send physiological saline for perfusion and a hole for accommodating small surgical tools. Thus, it must be relatively large in diameter (outer diameter: 3.5 mm). When it is to be inserted into pancreatic duct, which is smaller than bile duct, it is very difficult to place the tip of the insertion unit with outer diameter of 3.5 mm into the duct, and it requires skill. It is also very likely that the papilla is injured by the tip of the insertion unit.

The object of the present invention is to provide an endoscope for bile duct and pancreatic duct, in which the insertion unit of the daughter endoscope can be easily and safely inserted into papilla as well as into bile duct and pancreatic duct and the insertion unit of the daughter endoscope is used only for observation with no need for bending and for providing the path to send saline. Another object of the invention is to offer an endoscope for bile duct and pancreatic duct, in which it is possible to inject physiological saline for perfusion and also to insert various types of tools.

To achieve the objects as described above, the first invention consists of a mother endoscope having an insertion unit to be inserted into duodenum, a forceps channel of the insertion unit and an insertion hole connected with the forceps channel, of a flexible guide tube, which is to be inserted into bile duct and pancreatic duct from papilla through the forceps channel and into which the insertion unit of the daughter endoscope is inserted, and of a flexible core bar, which is mounted removably on one end of the guide tube, is inserted into the guide tube and has such length that its tip does not protrude from the guide tube. The second invention consists of a mother endoscope, of which the insertion unit having a forceps channel can be inserted into duodenum, and of a daughter endoscope, of which the insertion unit is guided by the flexible guide tube from the forceps channel of the mother endoscope and is inserted into bile duct and pancreatic duct. Two or more fixing tubes with different diameters are concentrically provided to cover the insertion unit on the base end of the insertion unit of the daughter endoscope, and the fixing tube corresponding to the guide tube, which is selected through an adaptor according to the diameter of a guide tube selected from two or more guide tubes having different diameters and inserted into bile duct and pancreatic duct from the forceps channel of the mother endoscope, is connected with the guide tube. The third invention consists of a flexible guide tube, which can be inserted into bile duct and pancreatic duct through the forceps channel through the insertion hole of the mother endoscope with its insertion unit placed into duodenum, of a fixing tube to be mounted on the base end of the insertion unit of the daughter endoscope, and of an adaptor, both ends of which are mounted on the fixing tube and on the guide tube, into which the insertion unit of the daughter endoscope is inserted. When the other end of the adaptor is mounted on the guide tube, the tip of the insertion unit inserted into the guide tube of the daughter endoscope is roughly aligned with the tip of the guide tube and does not protrude. Further, the fourth invention consists of a flexible first guide tube to be inserted from the insertion hole of the mother endoscope through the forceps channel into bile duct and pancreatic duct, of a junction tube to be connected with the first guide tube, of a flexible second guide tube, which has larger diameter than the first guide tube, is guided by the junction tube and the first guide tube and is inserted into bile duct and pancreatic duct, of a fixing tube to be mounted on the base end of the insertion unit, which is placed into the second guide tube of the daughter endoscope, of an enclosure unit provided on the base end of the insertion unit of the daughter endoscope to close up the gap between the fixing tube and the insertion unit of the daughter endoscope, and of an adaptor, both ends of which are mounted on the second guide tube and the fixing tube after the first guide tube and the junction tube have been withdrawn from the second guide tube, guided by the first guide tube and inserted into bile duct and pancreatic duct. It is provided at least with a cross passage in it and is designed in such manner that forceps or other tool and saline can be inserted or injected into bile duct and pancreatic duct through the second guide tube from the cross tube of the adaptor, comprising a straight tube and one or two or more cross tubes.

In the first invention, a core bar mounted on the mounting unit from the insertion hole of the mother endoscope is placed into the guide tube. This guide tube containing core bar is introduced into the forceps channel in order to insert the guide tube into bile duct and pancreatic duct. After observing duodenum and confirming the papilla by the tip of the insertion unit of the mother endoscope, the tip of the guide tube containing core bar is inserted into bile duct or pancreatic duct through papilla by manipulating the forceps elevator. Since a flexible core bar is contained in the guide tube, neither twisting nor turning occurs within the forceps channel, and positive insertion can be achieved straight toward the papilla. By fluoroscopy after the insertion, the core bar can be seen as image, and it is possible to confirm how far the guide tube has been inserted. If the core bar is withdrawn from the guide tube, it is possible to observe the interior of bile duct and pancreatic duct by placing the insertion unit of the daughter endoscope into the guide tube. In this case, it is possible to provide better observation through the supply of physiological saline through the gap between the insertion unit of the daughter endoscope and the guide tube.

When bile duct or pancreatic duct is observed by the second invention, the tip of the insertion unit of the mother endoscope is introduced perorally into duodenum and the position of papilla is confirmed. Then, a guide tube having such diameter that it is easy to insert into papilla is inserted into the forceps channel, and the tip of the guide tube is inserted again toward the papilla by utilizing the forceps elevator mounted on the tip of the insertion unit of the mother endoscope. Because the guide tube has full flexibility, it can be inserted into bile duct or pancreatic duct through papilla without injuring it. Also, the guide tube can be designed with smaller diameter because it is merely to accommodate the insertion unit of daughter endoscope for the purpose of observation only (neither the passage nor the forceps channel being required), and it can be inserted into papilla without difficulty. When the guide tube is inserted into bile duct or pancreatic duct through papilla, the insertion unit of the daughter endoscope is placed into the guide tube. Thus, physiological saline can be supplied through the gap between the insertion unit of daughter endoscope and the guide tube. In this case, an appropriate tube is chosen from two or more fixing tubes, and these tubes are connected through the adaptor, and saline is supplied by the use of this adaptor. Further, when a guide tube with larger diameter is used, the guide tube with larger diameter is inserted into bile duct and pancreatic duct using a guide tube of smaller diameter, and the latter is then withdrawn. A fixing tube corresponding to the guide tube with larger diameter is selected, and these tube are connected through adaptor to have communication with each other, and various types of tools can be inserted by utilizing the adaptor.

In the third invention, the papilla of duodenum is confirmed by the tip of the insertion unit of the mother endoscope. Then, the guide tube is introduced from the insertion hole into the forceps channel, and the tip of the guide tube is inserted toward papilla by manipulating the forceps elevator at the tip of the insertion unit. When the guide tube is inserted into bile duct or pancreatic duct through papilla, the insertion unit of the daughter endoscope is placed into the guide tube. When the other end of the adaptor is mounted on the guide tube, the tip of the insertion unit is roughly aligned with the tip of the guide tube. Hence, bile duct or pancreatic duct is not injured by the tip of fiberscope. Also, in order to ensure clear observation by the fiberscope, it is possible to inject physiological saline from the adaptor into the guide tube.

In the fourth invention, the papilla of duodenum is confirmed by the tip of the insertion unit of the mother endoscope. Then, the first guide tube with smaller diameter is placed from the insertion hole through the forceps channel, and the tip of the first guide tube is inserted toward papilla by manipulating the forceps elevator at the tip of the insertion unit. When the first guide tube is inserted into bile duct or pancreatic duct through papilla, the junction tube is connected with this first guide tube, and the second guide tube is inserted into bile duct or pancreatic tube, being guided by these tubes. Because the first guide tube has such diameter as to facilitate the insertion even into pancreatic duct, it is possible to insert it easily using the mother endoscope with narrower thinner forceps channel. The mother endoscope having the forceps channel with smaller diameter is withdrawn, and the junction tube and the first guide tube are inserted into the forceps channel of another mother endoscope having forceps channel of sufficiently larger diameter to accommodate the second guide tube. Thus, the mother endoscope can be replaced. Next, the insertion unit of the daughter endoscope can be placed into the second guide tube. When the other end of the adaptor is mounted on the second guide tube, injury to bile duct and pancreatic duct the tip of the insertion unit can be prevented through such arrangement that the tip of the insertion unit is roughly aligned with the tip of the second guide tube and does not protrude. Since the gap between the second guide tube and the insertion unit is relatively wide, a tool can be inserted or physiological saline can be supplied from the cross tube of the adaptor by utilizing this gap.

BRIEF DESCRIPTION OF THE DRAWINGS

FIG. 11 is a front view of the unit when junction tube is connected,

FIG. 12 is a cross-sectional view of the joint, and

FIG. 13 is a drawing to explain how the endoscope is inserted after mother endoscope is withdrawn.

FIG. 14 is a drawing to explain when the guide tube with larger diameter is inserted, and FIG. 15 explains how the insertion unit of the daughter endoscope is inserted.

FIG. 18 is a front view showing how the mounting unit is removed and core bar is withdrawn after the guide tube is inserted to the desired position in bile duct or pancreatic duct in the third invention, FIG. 19 is a front view showing how the insertion unit of the daughter endoscope is placed into the guide tube, and FIG. 20 is a cross-sectional view showing how the insertion unit of the daughter endoscope is mounted on the guide tube.

FIG. 22 is a front view showing how the mounting unit and the core bar are withdrawn after the first guide tube is placed into bile duct or pancreatic duct, FIG. 23 is a cross-sectional view of the portion where junction tube is connected, and FIG. 24 is a front view showing how the second guide tube is guided by the first guide tube and junction tube and is inserted into bile duct or pancreatic duct.

FIG. 25 is a front view showing how the first guide tube and the junction tube are withdrawn after the second guide tube has been placed into bile duct or pancreatic duct, and FIG. 26 is a front view showing how the insertion unit of daughter endoscope is placed into the second guide tube.

DESCRIPTION OF THE PREFERRED EMBODIMENTS

In the following, the present invention will be described in conjunction with the preferred embodiments.

Figure 1:
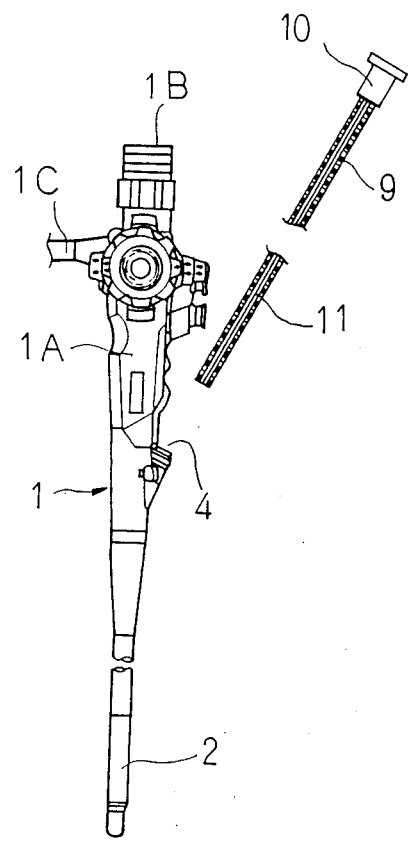
FIG. 1 is a schematical view showing the entire unit according to the first invention.
Figure 2:
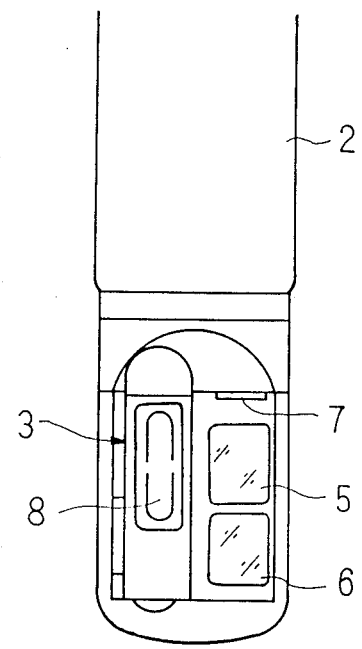
FIG. 2 is an enlarged view of the tip of the insertion unit.

FIG. 1 is a schematical view of the entire unit based on the first invention, where the mother endoscope (1) has an insertion unit (2), and the tip of the insertion unit (2) is placed into duodenum. The forceps channel (3) is formed in the insertion unit (2), and the base (1A) has the insertion hole on the forceps channel to receive various types of tools. The symbol (1B) represents an ocular unit of the mother endoscope, and (1C) is an optical cable connected with external light source equipment (now shown). As shown in FIG. 2, the tip of the insertion unit (2) is provided with an image guide window (5), a light guide window (6), a vent and water hole (7) and a forceps elevator (8) to bend the tool inserted from the forceps channel (3) to the desired direction. The forceps elevator (8) is operated by manipulating the base (1A). The optical cable (1C) sends light to the light guide window (6). A mounting unit (10) is removably mounted on one end of the flexible guide tube (9) inserted from the insertion hole (4) to the forceps channel (3), and the mounting unit (10) is furnished with a flexible core bar (11), which is placed into the guide tube (9) and its tip does not protrude from the guide tube (9).

Figure 3:
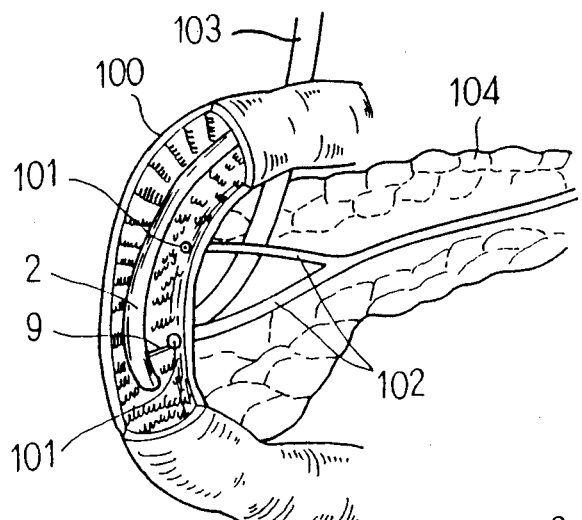
FIG. 3 is a drawing to explain how the guide tube is inserted into papilla.
Figure 4:
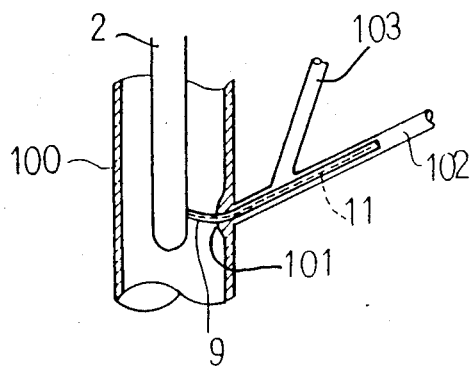
FIG. 4 is a cross-sectional view when the guide tube is inserted into pancreatic tube.

When the guide tube (9) is inserted into the papilla (101) of the duodenum (100), the insertion unit (2) of the mother endoscope (1) is first inserted into duodenum (100) perorally. After the position of papilla (101) has been confirmed by the ocular unit, the tip of the guide tube (9) is inserted into papilla (101) by manipulating the forceps elevator (8). The forceps channel (3) of the mother endoscope as used in this case has the diameter of 2.8 mm, and the diameter of the guide tube is 1.7 mm. In the pancreatic duct (102) adjoining the papillae (101) and (101), the upper accessory pancreatic duct is narrower and the lower major pancreatic duct is wider, whereas the guide tube (9) can be inserted into any of the papillae (101). Since the bile duct (103) is wider than pancreatic duct (102), any tube, which can be inserted into the pancreatic tube (102), can be easily inserted into bile duct (103). In FIG. 3, the symbol (104) indicates pancreas. FIG. 3 shows how the guide tube (9) is inserted into the papilla below (101), and FIG. 4 gives how the guide tube (9) has been inserted into the pancreatic duct (102). The flexible core bar (11) is placed into the guide tube (9), which is also flexible. Since the tip of the core bar (11) does not protrude from the tip of the guide tube (9), the guide tube (9) can be inserted smoothly within the pancreatic duct (102). In case the guide tube (9) is bent toward the papilla (101) at the forceps elevator (8), the direction of the tip of the guide tube (9) can be conveniently arranged because of the presence of core bar (11).

Figure 5:
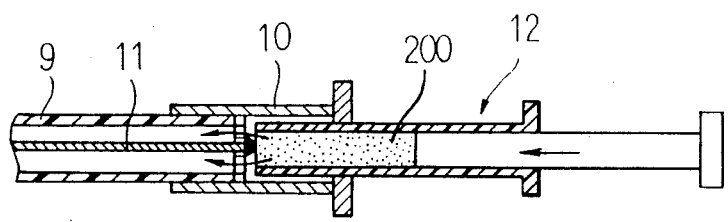
FIG. 5 is a cross-sectional view of an example of injection of contrast medium into guide tube.

If the guide tube (9) is inserted into the papilla (101) from the insertion hole (4) through the forceps channel (3), contrast medium (200) can be injected into the guide tube (9) by a syringe (12) connected with the mounting unit (10) as shown in FIG. 5. In injecting the contrast medium (200) into the guide tube (9), it is possible to inject it after removing the mounting unit (10) and withdrawing the core bar (11) from the guide tube (9) or to place it in the guide tube (9) in advance. Naturally, the syringe (12) is not necessarily used for the injection. When the guide tube (9) placed into the papillae (101) above and below is to be inserted further, it must be confirmed whether it has been inserted into the bile duct (103) or into pancreatic duct (102) or how far it has been inserted. Because the core bar (11) can be seen as image through fluoroscopy, it is possible to confirm to which of the ducts (103) and (102) or how far the tip of the guide tube (9) has been inserted.

Figure 6:
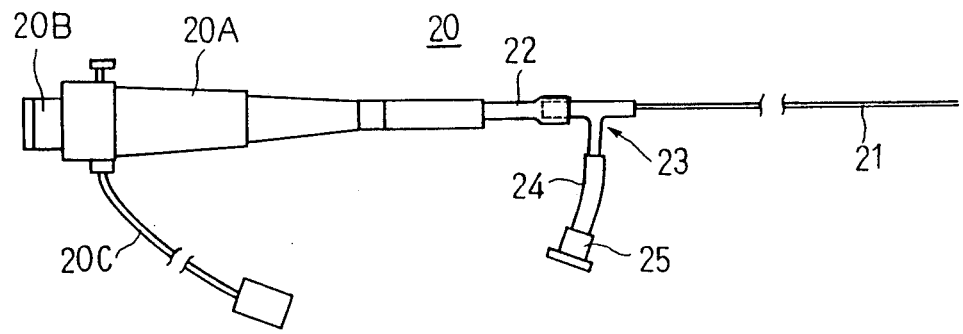
FIG. 6 is a schematical front view of the daughter endoscope.
Figure 7:
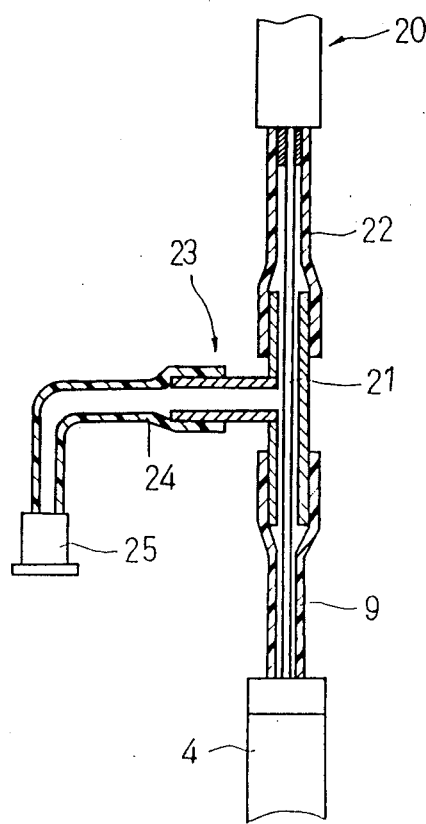
FIG. 7 is a cross-sectional view when the insertion unit of the daughter endoscope is inserted into the guide tube.

FIG. 6 shows the daughter endoscope (20) having the insertion unit (21) with diameter of 0.8 mm, which can be placed into the guide tube (9) inserted into the insertion hole (4) of the mother endoscope (1). This daughter endoscope (20) also possesses the base (20A), an ocular unit (20B) and an optical cable (20C) connected with external light source equipment (not shown). It is also furnished with a fixing tube (22), and one end of T-shaped adaptor (23) is connected with this fixing tube (22). The length of the insertion unit (21) exposed from the other end of this T-shaped adaptor (23) is shorter than the length of the guide tube (9). One end of the tube (24) is connected to this T-shaped adaptor (23), and a lure lock (25) is connected to the other end of the tube (24). As shown in FIG. 5, it is possible to inject physiological saline into the guide tube (9) from the lure lock, using the syringe (12). An application example of such daughter endoscope (20) is given in FIG. 7. Specifically, the guide tube (9) containing core bar (11) is inserted to the desired position in bile duct (103) or pancreatic duct (102). Then, the mounting unit (10) is removed and the core bar (11) is withdrawn, and the insertion unit (21) of the daughter endoscope (20) is placed into the guide tube (9). To the base protruding from the insertion hole (4) of the guide tube (9), the other end of T-shaped adaptor (23) is connected. When T-shaped adaptor (23) is connected with the guide tube (9), the length of the insertion unit (21) is shorter than the guide tube (9). Accordingly, the tip of the insertion unit (21) is roughly aligned with the tip of the guide tube (9) or a little recessed, and the tip of the insertion unit (21) does not protrude from the tip of the guide tube (9). Since there is a gap between the insertion unit

(21) and the guide tube (9), it is possible to supply physiological saline into this gap through the lure lock (25) and the tube (24). The daughter endoscope as used here needs not to have the function to bend or to provide the passage or forceps channel, and it needs only the function to observe. Therefore, the insertion unit (21) can be formed thinly as practically possible (as thin as 0.8 mm), and it is also possible to provide a gap between the guide tube (9) and the insertion unit (21) t supply saline.

As described above, it is possible by the first invention to removably mount the flexible core bar (11) on one end of the flexible guide tube, and the core bar is of such length that its tip does not protrude from the guide tube (9). The tip of the guide tube (9) containing core bar (11) is protruded from the tip of the insertion unit (2) which has been placed into duodenum (100) through forceps channel (3) from the insertion hole (4) of mother endoscope (1). Then, the tip of the guide tube (9) can be correctly directed toward the papilla (101) by manipulating the forceps stand (8), and the insertion into the papilla (101) is also easily achievable because core bar (11) is contained. Since it is the flexible guide tube (9) which comes into direct contact with the papilla (101) and with bile duct or pancreatic duct (103) or (102), there is no danger of injuring them. Because the guide tube (9) contains core bar (11) in it, it is neither twisted nor turned within the forceps channel (3) and can be inserted smoothly into bile duct or pancreatic duct (103) or (102). In fluoroscopy, the presence of the core bar (11) makes it possible to find out how far the guide tube (9) has been inserted. Further, it is possible to supply physiological saline through the guide tube (9) into bile duct or pancreatic duct (103) or (102).

Figure 8:
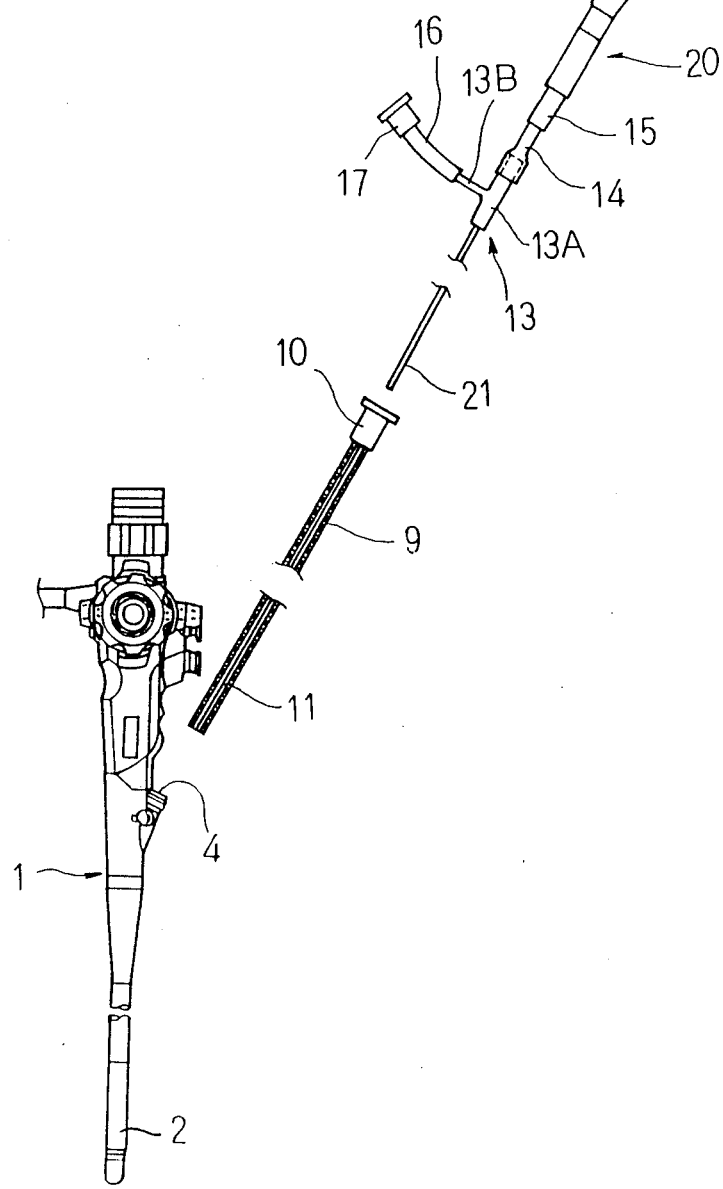
FIG. 8 is a view showing the outline of the unit according to the second invention.
Figure 9:
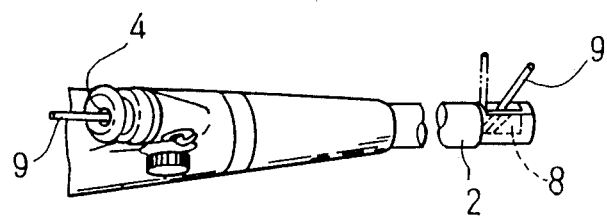
FIG. 9 is a perspective view when the guide tube is inserted into the forceps channel of mother endoscope.
Figure 10:
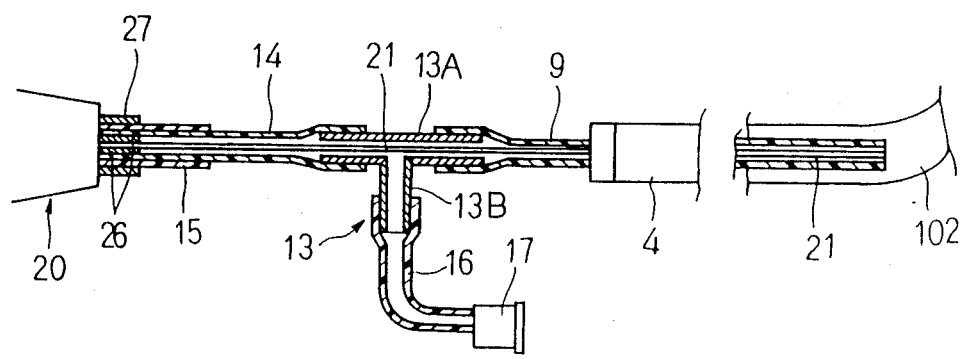
FIG. 10 is a cross-sectional view showing the details of the adaptor.

FIG. 8 shows schematically the entire unit based on the second invention, which consists of a mother endoscope having the insertion unit (2) to be inserted as far as duodenum (100), and of a daughter endoscope furnished with an insertion unit (21) to be inserted into bile duct or pancreatic duct (103) or (102) from the insertion hole (4) of the forceps channel (3), and with a guide tube (9) having smaller diameter. The tip of the insertion unit (2), which can be inserted into duodenum (100), is provided with an image guide window (5), a light guide window (6) and a vent and water hole (7), and with a forceps elevator (8) mounted on the forceps channel (3). When bile duct or pancreatic duct (103) or (102) is observed by the mother endoscope (1), the guide tube (9) and the daughter endoscope (20), the guide tube (9) is inserted into the forceps channel (3) from the insertion hole (4) of the mother endoscope (1). The mounting unit (10) is mounted on the base end of the guide tube (9), and the flexible core bar (11) is mounted on the mounting unit (10). The tip of the core bar (11) is designed in such manner as not to protrude from the tip of the guide tube (9). The papilla (101) of duodenum (100) is observed (see FIG. 3) by the tip of the insertion unit (2) of the mother endoscope (1), and the guide tube (9) is inserted into papilla (101) from the forceps channel (3). When the guide tube (9) is inserted into the papilla (101), the forceps elevator (8) is manipulated while observing through the mother endoscope (1), and the tip of the guide tube (9) is inserted into the papilla (101). Since the core bar (11) is contained in the guide tube (9), it is easier to insert the flexible guide tube (9) into the pancreatic duct (102) through papilla (101). When pancreatic duct (102) or bile duct (103) is photographed, the presence of the core bar (11) makes it possible to see how far the guide tube (7) has been inserted into the pancreatic duct (102) or bile duct (103). Also, it is possible to inject contrast medium into pancreatic duct (103) or bile duct (102) through the guide tube (9). The diameter of the guide tube (9) inserted into the pancreatic duct (103) or bile duct (102) is 1.7 mm. Core bar (11) is placed in the guide tube (9) because it contributes to the prevention of twisting in the forceps channel (3), to the easier insertion of guide tube (9) into the papilla (101) and also to the positive confirmation of the position of the tip by the image of core bar (11) by fluoroscopy. However, if the guide tube (9) is formed with such flexibility that it can be easily inserted into papilla (101) and if for clear imaging of the tip of the guide tube (9) by fluoroscopy metal power is coated thereon, there is no need to insert the core bar (11). When the guide tube (9) is placed from the insertion hole (4) of the mother endoscope (1) into forceps channel (3) and the tip of the guide tube (9) is inserted into pancreatic duct (102), the mounting unit (10) is removed and the core bar (11) is withdrawn from the guide tube (9). Then, the insertion unit (21) without the passage for saline or the forceps channel of the daughter endoscope (20) is inserted into the guide tube (9). When the insertion unit (21) is inserted into the guide tube (9) so that the tip of the insertion unit (21) of the daughter endoscope (20) is roughly aligned with the tip of the guide tube (9) and that the insertion unit (21) does not protrude from the tip of the guide tube (9), an adaptor (13) is furnished on the daughter endoscope to prevent the insertion unit (21) from excessive insertion. The adaptor (13) consists of a straight tube (13A) and a cross tube (13B), which is perpendicular to and connected with the straight tube (13A). One end of the straight tube (13A) is connected with a fixing tube (14) with smaller diameter selected from the fixing tubes (14) and (15) mounted on the daughter endoscope (20), and the other end of it is connected to the base end of the guide tube (9) (See FIGS. 8 and 10.). The cross tube (13B) of the adaptor (13) is connected with the tube (16), and physiological saline is supplied through this tube (16). Physiological saline is injected by the syringe, which is connected by the lure lock (17) mounted on the other end of the tube (16), and saline is sent into bile duct or pancreatic duct (103) or (102) through the gap between the insertion unit (21) and the guide tube (9) passing through the tube (16), the cross tube (13B) and the straight tube (13A). On the base end of the insertion unit (21) of the daughter endoscope (20), the fixing tubes (14) and (15) are concentrically provided, and the fixing tube (15) with larger diameter is to be used when another guide tube (18) and the adaptor (19) are used. This will be described later. Since the gap between the insertion unit (21) of the daughter endoscope (20) and the fixing tube (14) with smaller diameter is closed up at the base end of the insertion unit (21), an enclosure ring (26) is furnished, and also a fixing ring (27) is provided on the outermost periphery (See FIG. 10.).

Figure 16:
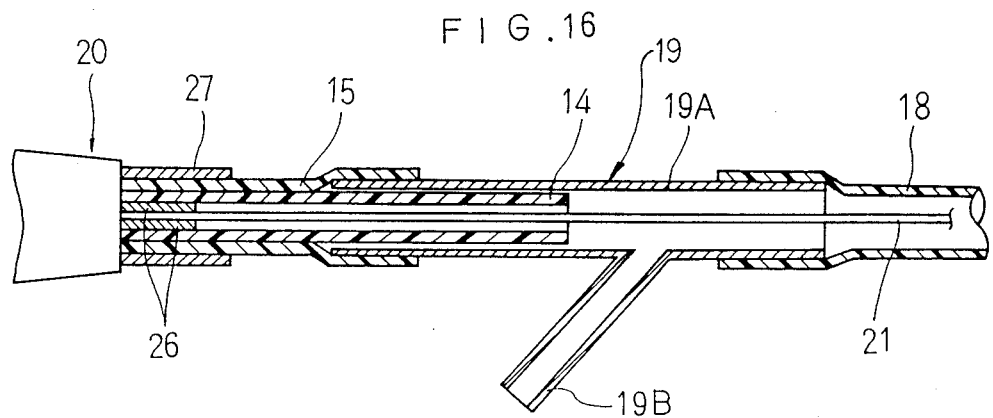
FIG. 16 is a cross-sectional view showing the details of the adaptor.
Figure 17:
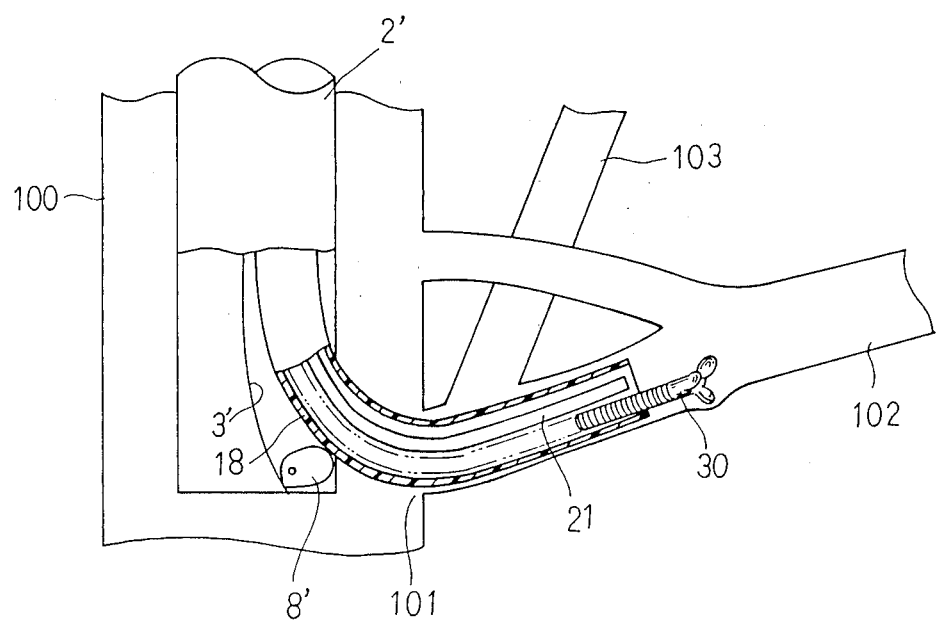
FIG. 17 shows how the forceps are inserted.
Figure 21:
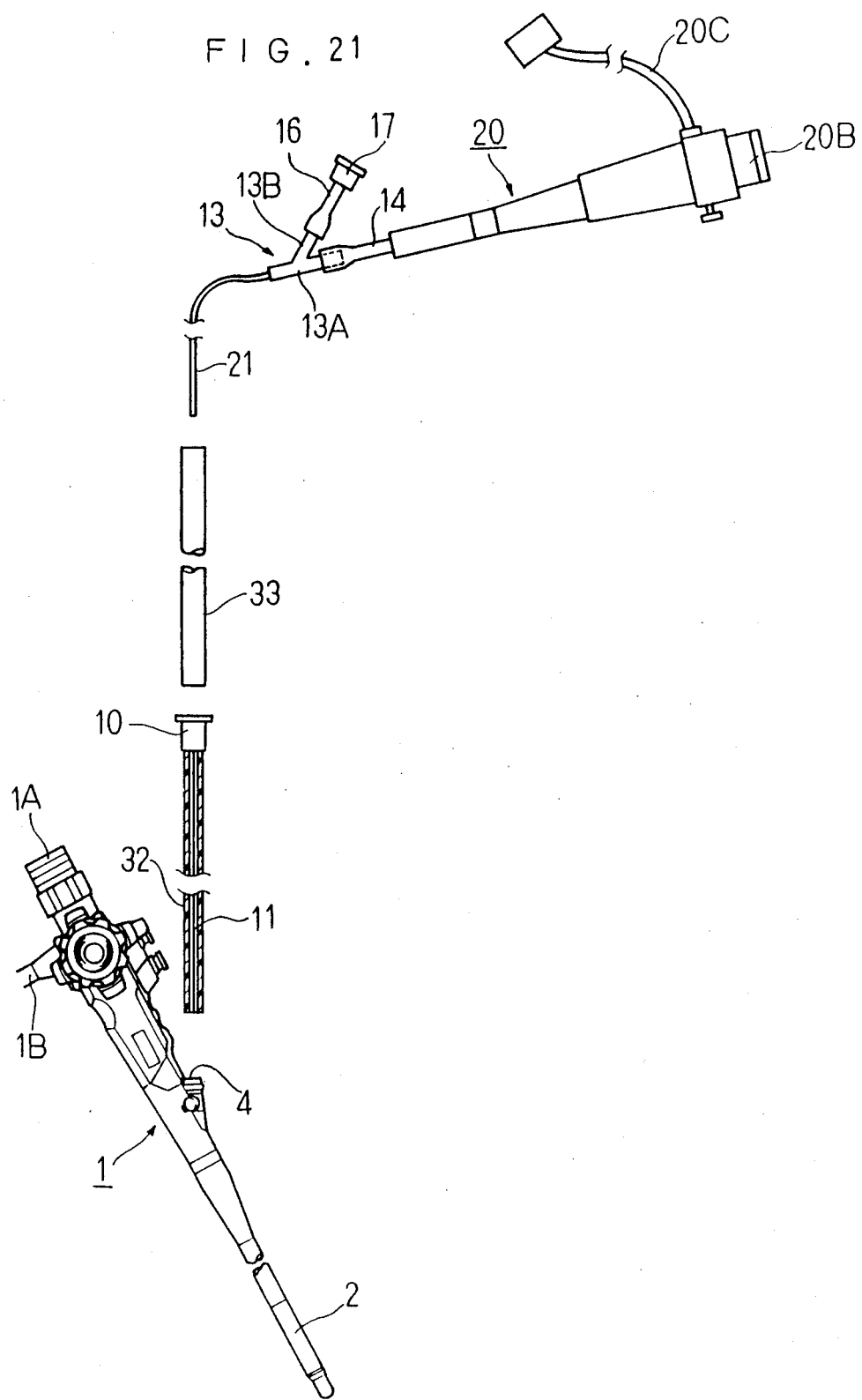
FIG. 21 is a schematical view of the entire unit according to the fourth invention.

Next, description will be given of the case where three endoscopes are used. When the guide tube (9) is inserted into bile duct and pancreatic duct (103) and (102), using the mother endoscope (1) and the guide tube (9), as described above, the guide tube (9) and the junction tube (29) with the same diameter are connected by a joint (28) as shown in FIG. 12 (see FIG. 11.). With both tubes (9) and (29) unchanged (with the tip of the guide tube (9) inserted into bile duct and pancreatic duct (102) and (103)), the mother endoscope (1) is withdrawn. Next, the endoscope (1') having the forceps channel (3') larger than the forceps channel (3) is inserted perorally into duodenum (100). Both tubes (9) and (29) are inserted into the forceps channel (3') and are taken out from the tube (29) through the insertion hole (4'). Then, guided by both tubes (9) and (29), the guide tube (18) with larger diameter is inserted into bile duct and pancreatic duct (103) and (102) (see FIG. 14). When the tip of the guide tube (18) is guided by the guide tube (9), already inserted into bile duct and pancreatic duct (103) and (102), the tubes (9) and (29) are withdrawn. When the tip of the insertion unit (2') of the endoscope (1') is inserted into duodenum (100) and the tip of the guide tube (18) is inserted into either bile duct (103) or pancreatic duct (102), the insertion unit (21) of the daughter endoscope (20) is inserted into the guide tube (18) through the adaptor (19) as shown in FIG. 15. One end of the straight tube (19A) of the adaptor (19) is connected to the fixing tube (15), and the other end to the guide tube (18). The details are as shown in FIG. 16, and the communicating portion of the cross tube (19B) is closer to the guide tube (18) than to the tip of the fixing tube (14). When this adaptor (19) is mounted on the daughter endoscope (20) and on the guide tube (18), it is designed in such manner that the tip of the insertion unit (21) is roughly aligned with the tip of the guide tube (18) and does not protrude. Through the gap between the guide tube (18) with larger diameter and the insertion unit (21), physiological saline can be supplied from the cross tube (19B) of the adaptor (19). Further, various types of tools can be accommodated such as forceps (30) as shown in FIG. 17. The endoscope (1'), which may be regarded as the mother of the mother endoscope (1), was used in this case, whereas it is possible to insert the guide tube (18) with larger diameter after inserting the guide tube (9) with smaller diameter, regarding the endoscope (1') as the mother from the beginning.

As described above, two or more guide tubes (9) and (18) are used in the second invention, and after the guide tube (9) with smaller diameter is first inserted into bile duct and pancreatic duct (103) and (102), the insertion unit (21) of the daughter endoscope (20) is placed into this guide tube (9). This makes it possible to insert the insertion unit (21) into bile duct and pancreatic duct (103) and (102) in safe and easier manner. Also, the guide tube (18) with larger diameter can be smoothly inserted into bile duct and pancreatic duct (103) and (102) because it is guided by the guide tube (9) with smaller diameter. When any of these guide tubes (9) and (18) are inserted, the guide tubes (9) and (18) can be connected with the fixing tubes (14) and (15) mounted on the base of the insertion unit (21) of the daughter endoscope (20) through the adaptor (19). If designed well, the tip of the insertion unit (21) does not protrude from the tip of the guide tubes (9) or (18), and it is possible to supply physiological saline or to insert various types of tools from the adaptor into the guide tubes (9) or (18).

Next, the preferred embodiments based on the third invention will be described in conjunction with FIGS. 18 to 20.

The third invention is also provided with the same configuration as shown in FIG. 8. If the guide tube (9) is inserted to the desired position as shown in FIG. 3 in such endoscope system, the mounting unit (10) is removed and the core bar (11) is withdrawn from the guide tube (9) as shown in FIG. 18. Then, the insertion unit (21) of the daughter endoscope (20) is placed into the guide tube (9), which is protruding from the insertion hole (4) (see FIG. 19.). The other end of the straight tube (13A) of the adaptor (13) is then mounted on the guide tube (9). As shown in FIG. 20, the tip of the insertion unit (21) of the daughter endoscope (20) is roughly aligned with the tip of the insertion unit (21) of the daughter endoscope (20), and the tip of the insertion unit (21) does not protrude from the tip of the guide tube (9). With this adaptor (13) mounted on the guide tube (9), the insertion unit (21) cannot be inserted further into the guide tube (9). When bile duct (103) or pancreatic duct (102) is observed with the insertion unit (21) of the daughter endoscope (20) placed into the guide tube (9), the observation by the insertion unit (21) can be performed more conveniently and clearly if physiological saline is supplied to bile duct (103) or pancreatic duct (102) by such means as the syringe (31) through the tube (16) and the lure lock (17) mounted on the cross tube (13B) of the adaptor (13). Since the insertion unit (21) requires neither a passage for saline nor a mechanism to bend the tip nor a forceps channel, its outer diameter can be designed as small as 0.8 mm.

The diameter of the forceps channel (3) of the mother endoscope (1) was set to 2.8 mm in this case, the diameter of the guide tube (9) to 1.7 mm, and the diameter of the insertion unit (21) to 0.8 mm. Outer diameter of the guide tube (9) used in the present invention can be set to about 1.7 mm. Thus, its tip can be smoothly inserted into the papilla (101) and also into pancreatic duct (102), which is smaller in diameter than bile duct (103).

As explained above, it is possible by the third invention to easily insert the guide tube (9), having such diameter as to facilitate the insertion into papilla, into bile duct (103) or pancreatic duct (102) through the papilla (101), and there is no danger of injuring the papilla (101) and the like. When the guide tube (9) is inserted into bile duct (102) or pancreatic duct (103) through papilla (101) in easy and safe manner, the insertion unit (21) can be easily guided into bile duct (102) or pancreatic duct (103) only by placing the insertion unit (21) of the daughter endoscope (20) into the guide tube (9). In placing the insertion unit (21), the adaptor (13) serves as a stopper. Even when the insertion unit (21) is inserted to full extent, its tip does not protrude from the tip of the guide tube (9), and the risk of injuring bile duct (103) or pancreatic duct (102) is thus eliminated. Further, it is also possible to inject physiological saline into the guide tube (9) from the cross tube by utilizing the adaptor (13), and this ensures clear observation by the daughter endoscope (20).

Figure 27:
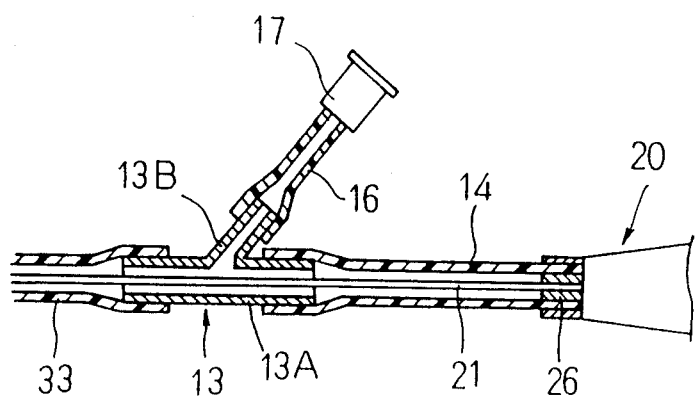
FIG. 27 is a cross-sectional view showing how the insertion unit of the daughter endoscope is mounted on the second guide tube.

The embodiment according to the fourth invention as shown in FIGS. 21 to 32 consists of a mother endoscope (1) having a forceps channel (3) on the insertion unit (2) placed into duodenum (100), a first guide tube (32), inserted into the forceps channel (3) from the insertion hole (4) connected to the forceps channel (3) of the mother endoscope (1), a second guide tube (33), the diameter of which is larger than that of the first guide tube (32) and in which the first guide tube (32) can be inserted, and a daughter endoscope (20) having an insertion unit (21), which can be inserted into bile duct (103) or pancreatic duct (102). The insertion unit (2) of the mother endoscope (1) can be perorally inserted to duodenum (100), and inner diameter of the forceps channel (3) is set to 3.7 mm. As shown in FIG. 2, the tip of the insertion unit (2) of this mother endoscope (1) is furnished with an image guide window (5), a light guide window (6), a vent and water hole (7) and a forceps elevator (8) mounted on the forceps channel (3). On one end of the flexible first guide tube (32), a mounting unit (10) is removably mounted, and the flexible core bar (11) to be inserted into the first guide tube (32) is mounted on this mounting unit (10). The tip of this core bar (11) is of such length that it does not protrude from the tip of the guide tube (32). The daughter endoscope (20) is provided with an ocular unit (20B) and an optical cable (20C) connected to the external light source equipment (not shown). A fixing tube (14) is mounted on the base, and one end of the adaptor (13) is mounted on this fixing tube (14). The adaptor (13) consists of a straight tube (13A) and a cross tube (13B) crossing with the straight tube (13A). The tube (16) is mounted on the cross tube (13B), and a lure lock (17) is mounted on this tube (16). As explained above, the forceps channel (3) of the mother endoscope (1) has inner diameter of 3.7 mm, and the first guide tube (32) has outer diameter of 1.7 mm. When the insertion unit (2) of such mother endoscope (1) is inserted into duodenum (100) and the position of the papilla (101) is confirmed by the tip of the insertion unit (2), the first guide tube (32) is passed through the forceps channel (3) from the insertion hole (4), and its tip is inserted into papilla (101) by manipulating the forceps elevator (8). To find out to which of bile duct (103) or pancreatic duct (102) the first guide tube (32) from papilla has been inserted, the core bar (11) can be clearly identified by fluoroscopy. Also, it is possible to photograph by injecting contrast medium into the first guide tube (32) Thus, when the first guide tube (32) has been inserted to the desired position in bile duct (103) or pancreatic duct (102), the mounting unit (10) is removed and the core bar (11) is withdrawn, leaving only the first guide tube (32) as shown in FIG. 22. The first guide tube (32) is connected with the junction, tube (29) having the same diameter through a joint (28) (see FIG. 23). Guiding the flexible second guide tube (33) by means of the first guide tube (32) as shown in FIG. 24, the second guide tube (33) is inserted into bile duct (103) or pancreatic duct (102). When the second guide tube (33) is inserted into bile duct (103) and pancreatic duct (102) in this way, the first guide tube (32) and the junction tube (29) are withdrawn as shown in FIG. 25. Then, the insertion unit (21) of the daughter endoscope (20) is placed into the second guide tube (33). The insertion unit (21) is stopped when the other end of the straight tube (13A) of the adaptor (13) is mounted on the second guide tube (33). In this status, as shown in FIG. 27, the tip of the insertion unit (21) is roughly aligned with the tip of the second guide tube (33) and does not protrude. The gap between the fixing tube (14) mounted on the base of the daughter endoscope (20) and the insertion unit (21) is closed up by the enclosure ring (26). Accordingly, even when fluid or tool is placed in the gap between the second guide tube (33) and the insertion unit (21) by means of the cross tube (13B), the fluid will not flow along toward the operator because it is blocked by the enclosure ring (26).

Figure 28:
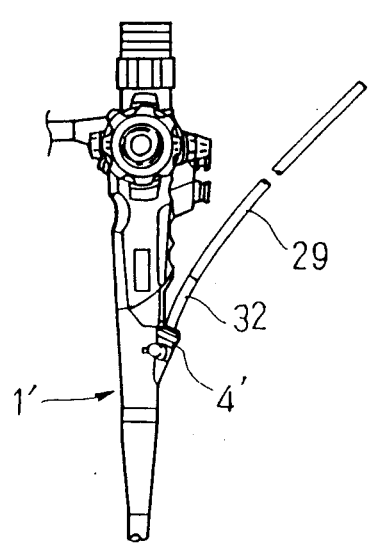
FIG. 28 is a front view showing how the first mother endoscope is withdrawn.
Figure 29:
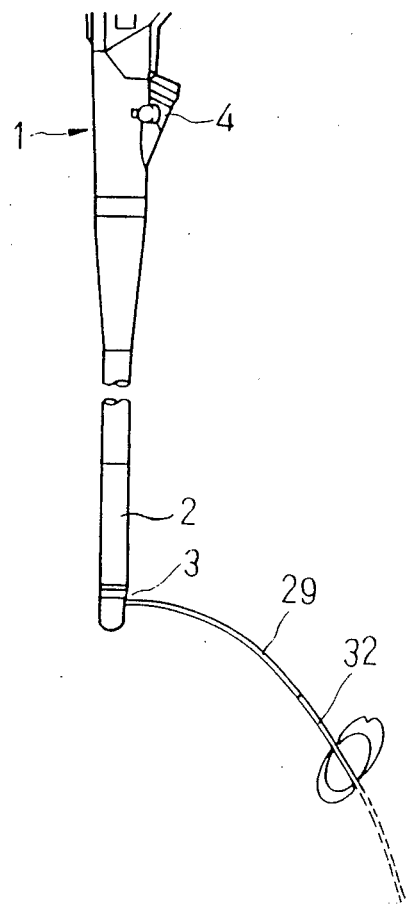
FIG. 29 is a front view explaining how the insertion unit of the mother endoscope is inserted after the first mother endoscope is withdrawn.
Figure 30:
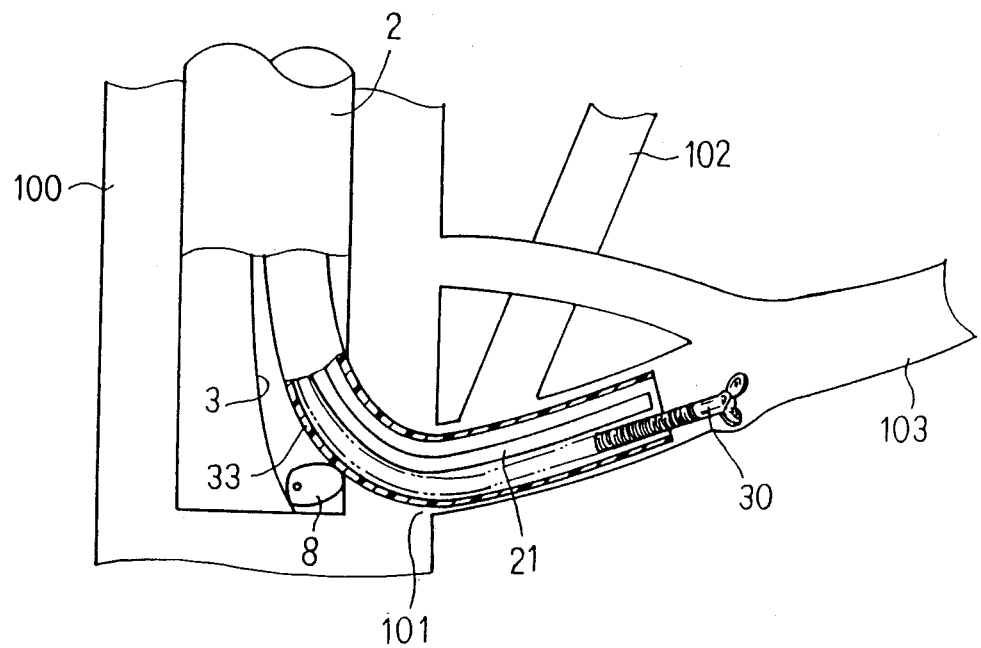
FIG. 30 is a cross-sectional view when daughter endoscope is connected with mother endoscope and forceps are inserted into pancreatic duct from the adaptor.

In the embodiment as described above, inner diameter of the forceps channel (3) of the mother endoscope was set to 3.7 mm. However, when the first guide tube (32) with diameter of 1.7 mm is placed into the forceps channel (3) with inner diameter of 3.7 mm and is inserted into bile duct (103) or pancreatic duct (102), the insertion will be difficult because there is too much free space between the first guide tube (32) and the forceps channel (3). Accordingly, the first mother endoscope (1') having the forceps channel (3) with inner diameter of 2.8 mm is used as shown in FIG. 28, and the first guide tube (32) is inserted from the insertion hole (4') into bile duct (103) and pancreatic duct (102) according to the procedure as described above, and the junction tube (29) is connected to the first guide tube (32) protruding from the insertion hole (4') through the joint (28). When the junction tube (29) is connected, the first endoscope (1') is withdrawn from the first guide tube (32) and the junction tube (29). Then, it is inserted into the tip of the insertion unit (2) of the mother endoscope (1) (the second mother endoscope) through the forceps channel with inner diameter of 3.7 mm, and this insertion unit (2) is inserted into duodenum (100) (see FIG. 29). Thus, after the first mother endoscope (1') is replaced with the second mother endoscope (1), the second guide tube (33) is inserted into bile duct (102) or pancreatic duct (103), being guided by the junction tube (29) and the first guide tube (32). The subsequent procedure is as described above. When the mother endoscope (1) having the forceps channel (3) with inner diameter of 3.7 mm is inserted into duodenum (100), the forceps (30) are inserted from the cross tube (13B) of the adaptor (13). Then, the forceps (30) are placed into pancreatic duct (103) through the gap between the second guide tube (33) and the insertion unit (21), which is shown in FIG. 30.

Figure 31:
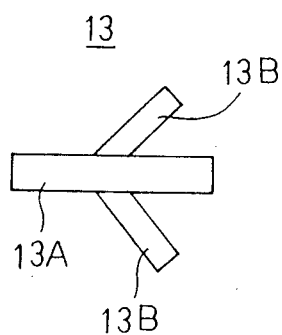
FIGS. 31 and 32 are the front views showing the variations of the adaptor.
Figure 32:
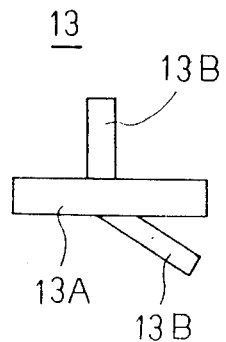

The adaptor (13), the respective ends of straight tube (13A) portion of which are mounted on the fixing tube (14) and the second guide tube (33), may be provided with cross tubes (13B) connected to the straight tube (13A) as shown in FIG. 31 and FIG. 32; moreover, the adaptor (13) need not be a Y-shaped unit with a 3-way path in it and more than two cross tubes (13B) may be provided. In the adaptor (13), where two or more cross tubes (13B) are provided, the forceps (30) or other tools are inserted from one of the cross tubes (13B), and physiological saline may be injected from the other cross tube (13B).

As described above, the first guide tube (32) with smaller diameter is first placed into bile duct (103) or pancreatic duct (102) through the papilla (101) by the fourth invention, and the first guide tube (32) with smaller diameter is connected with the junction tube (29). Then, guided by these tubes (29) and (32), the second guide tube (33) with larger diameter is inserted into bile duct (103) or pancreatic duct (102). Therefore, the insertion is easily achievable and the flexibility of the first and second guide tubes (32) and (33) prevent injury to bile duct (103) or pancreatic duct (102) as well as papilla (101). When it is desired not only to observe bile duct (103) or pancreatic duct (102) but also to perform surgical procedure, the second guide tube (33) can be inserted into bile duct (103) or pancreatic duct (102), guided by the first guide tube (32) and the junction tube (29). Since the first guide tube (32) is already inserted into bile duct (103) or pancreatic duct (102) in such case, even the second guide tube (33) with larger diameter can be smoothly inserted into bile duct (103) or pancreatic duct (102). After the second guide tube (33) is inserted, the first guide tube (32) and the junction tube (29) are withdrawn, and the other end of the adaptor (13) of the daughter endoscope (20) is mounted on this second guide tube (33). This makes it possible to insert forceps (30) or other tool into the second guide tube (33) from the cross tube (13B) of the adaptor (13). Thus, the observation and surgical procedure of bile duct (103) or pancreatic duct (102) can be easily achieved. Further, if physiological saline is injected from the cross tube (13B) of the adaptor (13), the regions can be observed more clearly.

I claim:

1. An endoscope for bile duct and pancreatic duct comprising a mother endoscope, and a daughter endoscope having an insertion unit, the mother endoscope having an insertion unit to be inserted into duodenum, a forceps channel in said insertion unit and an insertion hole communicating with the forceps channel, a flexible guide tube having flexibility to be inserted into bile duct and pancreatic duct from papilla through the forceps channel from the insertion hole and into which the insertion unit of the daughter endoscope is inserted, and a flexible core bar mounted removably on one end of and received in the guide tube, having a tip at its end remote from said one end of the guide tube and being of such length that the tip does not protrude from the tube.

2. An endoscope for bile duct and pancreatic duct, comprising a mother endoscope having an insertion unit, a daughter endoscope having an insertion unit, the mother endoscope having a forceps channel in its insertion unit and an insertion hole communicating with the forceps channel, and a flexible guide tube having a remote end to be inserted into bile duct and pancreatic duct through the forceps channel from the insertion hole of the mother endoscope, of which the insertion unit is inserted into duodenum, wherein the endoscope further comprises a fixing tube to be mounted on the base end of the insertion unit of the daughter endoscope, and an adaptor, respective ends of which mate with the fixing tube and the guide tube, into which an end of the insertion unit of the daughter endoscope is inserted, the other end of the insertion unit of the daughter endoscope being a free tip, wherein the adaptor is so dimensioned that it does not fit into the guide tube and said tip of the insertion unit of the daughter endoscope is roughly aligned with the tip of the remote end of the guide tube and does not protrude therefrom when the adaptor abuts against the guide tube.

3. An endoscope for bile duct and pancreatic duct comprising a mother endoscope and a daughter endoscope, the mother endoscope having an insertion unit to be inserted into duodenum, a forceps channel in said insertion unit and an insertion hole communicating with the forceps channel, and the daughter unit having an insertion unit for insertion into bile duct or pancreatic duct, a flexible first guide tube to be inserted into bile duct or pancreatic duct through the forceps channel from the insertion hole of the mother endoscope, a junction tube connected with the first guide tube, a flexible second guide tube of diameter larger than that of the first guide tube and to be inserted into bile duct or pancreatic duct, being guided by the junction tube and the first guide tube, a fixing tube to be mounted on the base end of the insertion unit, which is inserted into the second guide tube of the daughter endoscope, an enclosure unit mounted on the base end of the insertion unit of the daughter endoscope to close up the gap between the fixing tube and the insertion unit of the daughter endoscope, and an adaptor in which is provided an at least 3-way path, the adaptor comprising a straight tube and at least one cross tube communicating with the straight tube, respective ends of the straight tube of the adaptor being mounted on the second guide tube and the fixing tube after the first guide tube and the junction tube are withdrawn from the second guide tube, which has been guided by the first guide tube and has been inserted into bile duct or pancreatic duct, surgical tools such as forceps of physiological saline and the like being insertable or injectable into bile duct or pancreatic duct through the second guide tube from a said cross tube of the adaptor.

4. An endoscope for bile duct and pancreatic duct, comprising a mother endoscope having an insertion unit to be inserted into duodenum, the insertion unit being provided with a forceps channel, and a daughter endoscope having an insertion unit to be inserted into bile duct and pancreatic duct, wherein the endoscope further comprises a plurality of alternative flexible guide tubes of different diameters for guiding the insertion unit of the daughter endoscope through the forceps channel of the mother endoscope into bile duct and pancreatic duct, a plurality of alternative adaptors of different diameters, each of the adaptors being tubular and having opposed ends, each of the adaptors being adapted to mate at one of said opposed ends with a respective one of the guide tubes, and a plurality of concentric fixing tubes of different diameters, each of the fixing tubes being adapted to mate with the other opposed end of a respective one of the adaptors and, thereby, through the adaptor, connect the insertion unit of the daughter endoscope to the rest of the daughter endoscope.

* * * * *